United States Patent [19]

Kawasaki

[11] Patent Number: 5,001,674
[45] Date of Patent: Mar. 19, 1991

[54] ULTRASONIC TESTING METHOD

[75] Inventor: Keiji Kawasaki, Nagoya, Japan

[73] Assignee: NGK Insulators, Ltd., Aichi, Japan

[21] Appl. No.: 454,404

[22] Filed: Dec. 21, 1989

[30] Foreign Application Priority Data

Dec. 21, 1988 [JP] Japan ............................. 63-322858
Dec. 21, 1988 [JP] Japan ............................. 63-322859

[51] Int. Cl.⁵ .................. H04B 17/00; G01N 29/00; G01N 29/04; G01N 29/24
[52] U.S. Cl. ........................................ 367/13; 73/640; 73/642; 310/336
[58] Field of Search .................. 367/13; 73/629, 632, 73/640, 642; 310/336

[56] References Cited

U.S. PATENT DOCUMENTS

| 4,041,774 | 8/1977 | Morris et al. | 73/67.9 |
| 4,472,975 | 9/1984 | Beck et al. | 73/642 |
| 4,566,333 | 1/1986 | Chubachi et al. | 73/629 |

FOREIGN PATENT DOCUMENTS

| 0042601 | 12/1981 | European Pat. Off. |
| 0064399 | 11/1982 | European Pat. Off. |
| 0146707 | 7/1985 | Euroepan Pat. Off. |
| 0191346 | 8/1986 | European Pat.Off. |

OTHER PUBLICATIONS

Japanese Journal of Applied Physics, vol. 24, Suppl. No. 24, part 1, 1985, pp. 100-102, A. Jitsumori et al; et al: "Detection of Near-Surface Flaws Using Linear FM Ultrasonic Wave".

Primary Examiner—Ian J. Lobo
Attorney, Agent, or Firm—Parkhurst, Wendel & Rossi

[57] ABSTRACT

An ultrasonic testing method comprises steps of transmitting an ultrasonic wave from a probe to a test article, detecting an internal flaw in the test article by a reflected flaw echo from the internal flaw, and deciding a condition of the detected flaw by comparing and analyzing frequency components of the transmitted ultrasonic wave and the reflected flaw echo. The probe has a curved tip surface which is the same kind as that of a curved incident surface of the test article and has a radius of curvature of 0.5~2.0 times the radius of curvature of the curved incident surface of the test article.

3 Claims, 4 Drawing Sheets

FIG_1
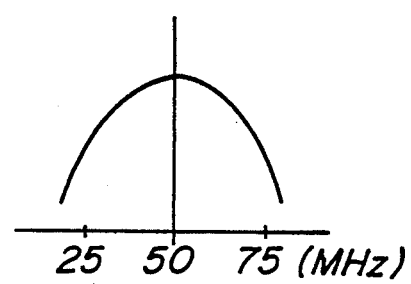
FIG_2
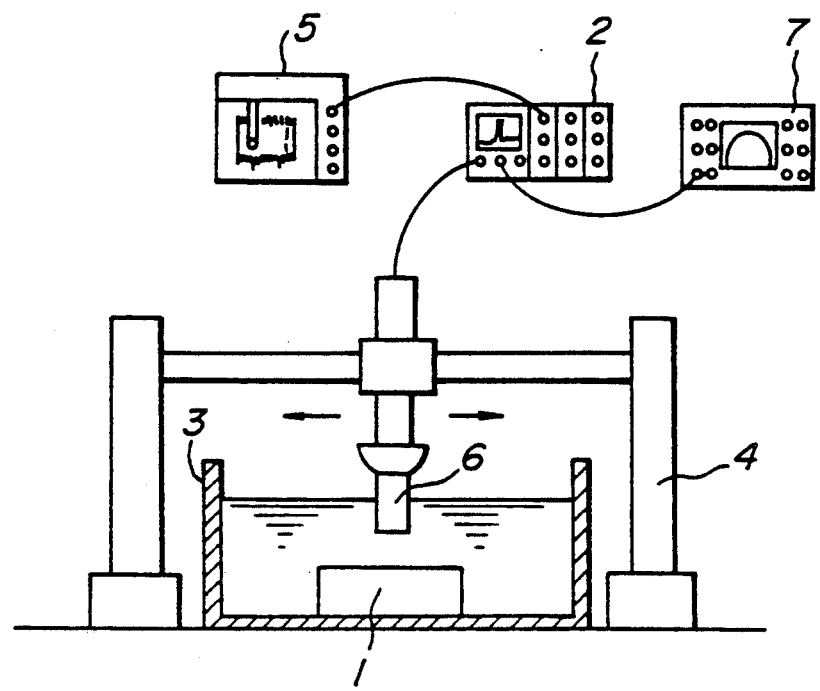

FIG._3
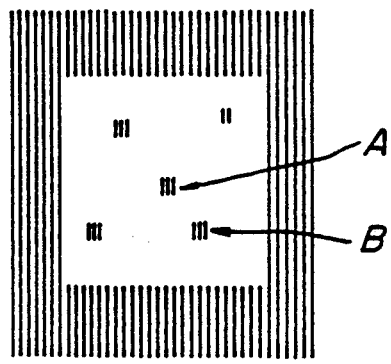
FIG._4
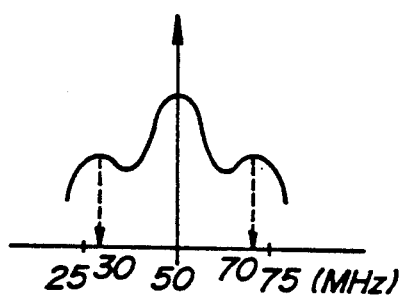
FIG._5
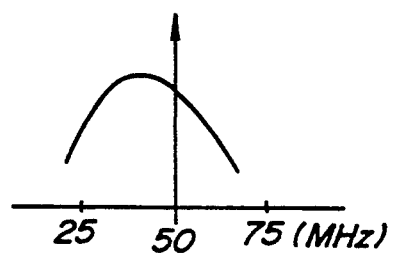
FIG._6a
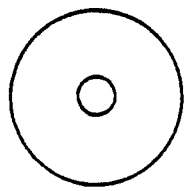
FIG._6b
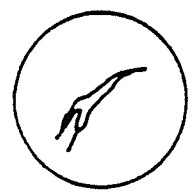

FIG_7
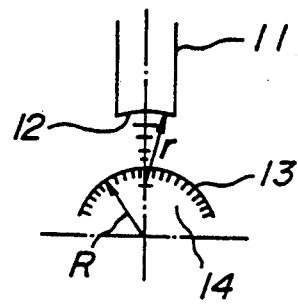
FIG_8a
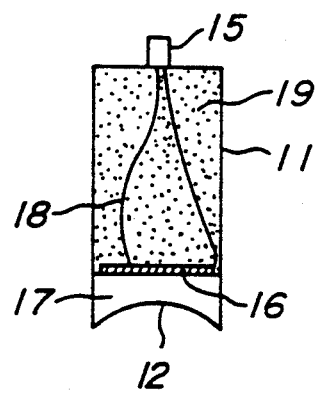
FIG_8b
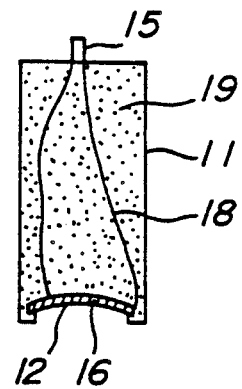

ULTRASONIC TESTING METHOD

BACKGROUND OF THE INVENTION

1. Field of the Invention

The present invention relates to an ultrasonic testing method for detecting an internal flaw of articles.

2. Related Art Statement

The ultrasonic test has been generally used for detecting an internal flaw in steel members, steel sheets or plates, welded portions, machine parts and other articles. Recently, the ultrasonic test also has been used for detecting an internal flaw in ceramics and like new materials. However, the conventional ultrasonic testing method decides a condition of a detected flaw of a test article by presuming a size of the flaw from a size of a flaw echo reflected from the flaw measured by means of an oscilloscope or the like, or by presuming a size of the flaw from a size of a two dimensional indication of the flaw detected by automatically scanning the test article. However, even if the internal flaws in the test articles are the same in size, influences on strength of the articles are entirely different dependent on the condition of the flaws. Particularly, in a brittle material such as ceramics, the influences of flaws are remarkably different dependent on the condition of flaws and therefore there was a problem with presuming the condition of the flaw by only the size of the indication. For example, when the flaw is decided on only the size, an article having a flaw which is in large size but does not actually affect the strength of the article is rejected, on the contrary, an article having a crack of small size, but having a problem on the strength is accepted.

Furthermore, in the conventional ultrasonic testing method, an immersing prove having a simple plane transducer has been used for transmitting an ultrasonic wave to a test article immersed in water such as a steel member, steel sheet, forged article or the like, since the test article is relatively large and the flaw also is larger than several millimeters. Moreover, there has been used a focusing probe having a transducer provided with a concave resin lens or a transducer formed into a concave shape in order to detect a flaw of several hundred mm, when the article requires a high reliability. Recently, there have been developed high reliable articles made of brittle structural materials such as ceramics to be used under a severe circumstance. Accordingly, it is desired to establish a high analyzable testing method for deciding the internal flaw in the articles In the ultrasonic test for detecting the internal flaw in ceramic article or the like, use is made of an ultrasonic wave of a high frequency such as 15 ~ 100 MHz higher than the conventional testing ultrasonic wave of 0.5 ~ 10 MHz, and a computer is also frequently used for processing wave patterns.

However, the prior art technique mentioned above can be applied only to articles having simple configurations such as a flat sheet or plate, cylindrical body, and cylindrical surface, but articles having a curved surface, particularly curved surface of a radius of curvature not larger than 10 mm is less detectable. For example, when the conventional probe having the flat transducer or the focusing probe is applied to the curved surface having a small radius of curvature, the ultrasonic wave is scattered at the incident curved surface so that the flaw is not detected There are recently developed ceramic articles such as balls for bearing and ceramic parts for engines and gas turbine, and therefore a testing method for effectively detecting these articles having a curved surface of a small radius of curvature is desired.

SUMMARY OF THE INVENTION

An object of the present invention is to eliminate the above mentioned disadvantage of the conventional ultrasonic testing method, and to provide an improved ultrasonic testing method for effectively detecting the internal defect in a test article, and further for effectively deciding the condition of the detected flaw.

Thus, the inventor conducted assiduous studies on an ultrasonic testing method adapted for analyzing a condition of a flaw detected by the ultrasonic test and deciding whether the body containing the detected flaw is acceptable for use or not, and has found that the condition of the flaw can be decided by analyzing a frequency component of a flaw echo, and thus has reached the present invention.

Therefore, according to the first aspect of the present invention, in an ultrasonic testing method comprising steps of transmitting an ultrasonic wave to a test article, and detecting an internal flaw in the test article by a reflected flaw echo from the internal flaw, frequency components of an incident ultrasonic wave transmitted to the test article and a reflected flaw echo are compared and analyzed to decide conditions of a flaw in the test article.

According to the present invention, frequency components of the flaw echo reflected from a portion of the test article corresponding to an indication of the detected flaw are compared and analyzed by means of a spectrum analyzer or the like to decide whether the condition of flaw is a spherical hole the a crack. For example, when an ultrasonic wave transmitted from a probe is a testing frequency of 50 MHz, the ultrasonic wave contains frequency components of ±30 MHz to the central frequency of 50 MHz as shown in FIG. 1. When the transmitted incident ultrasonic wave is reflected on a flat shaped flaw, frequency components of the reflected echo is substantially the same as the frequency components of the transmitted incident ultrasonic wave. While, when the transmitted incident ultrasonic wave is reflected on a crack flaw, the high frequency component of the reflected echo is scattered and reduced to be smaller, and when the transmitted incident ultrasonic wave is reflected on a spherical flaw such as a hole, the ultrasonic wave is reflected and transformed in mode on the surface of the flaw. As a result such a transformed echo contained in the reflected echo has peaks at the central frequency as well as at the low and high frequency sides thereof.

As aforementioned, according to the first aspect of the present invention, the condition of the flaw can be decided by analyzing the echo frequency component reflected from the internal flaw in the test body by means of a frequency analyzer such as a spectrum analyzer.

The inventor also conducted experiment and studies on an ultrasonic testing method adapted for articles having a curved surface of a small radius o curvature not larger than several tens of millimeters and has reached the present invention.

Therefore, according to the second aspect of the present invention, in an ultrasonic testing method for detecting an internal flaw in a test article having a curved surface, use is made of a probe provided with a probe tip having the same curved tip surface as that of the test article, and a radius of curvature of the curved tip surface of 0.5 ~2.0 times the radius of curvature of the curved article surface.

According to the second aspect of the present invention, a probe having a curved tip surface corresponding with the curved surface of the test article is used. For example, when the curved surface of the article to be tested is a spherical surface, a probe provided with a tip such as an acoustic lens or transducer having a spherical surface is used, and when the surface of the article to be tested is a cylindrical surface, a probe provided with a tip such as an acoustic lens or transducer having a cylindrical surface is used. Thus, the transmitted ultrasonic wave does not scatter on the curved incident surface of the test article, and consequently, the internal flaw in the test article having a curved incident surface of a radius of curvature not more than several ten of millimeters can be effectively detected The invention now will be described more in detail with reference to the accompanying drawings

BRIEF DESCRIPTION OF THE DRAWINGS

FIG. 1 shows a waveform of a frequency component;

FIG. 2 is a diagrammatic view illustrating an ultrasonic testing apparatus;

FIG. 3 is a diagrammatic view of plotter showing results of ultrasonic tests;

FIGS. 4 and 5 show waveforms of frequency components;

FIGS. 6a and 6b are diagrammatic views illustrating internal flaws in test articles;

FIG. 7 is a diagrammatic view illustrating a probe positioned relatively to a test article;

FIGS. 8a and 8b are diagrammatic sectional views illustrating a probe in different conditions;

DESCRIPTION OF THE PREFERRED EMBODIMENTS

Figure 9:
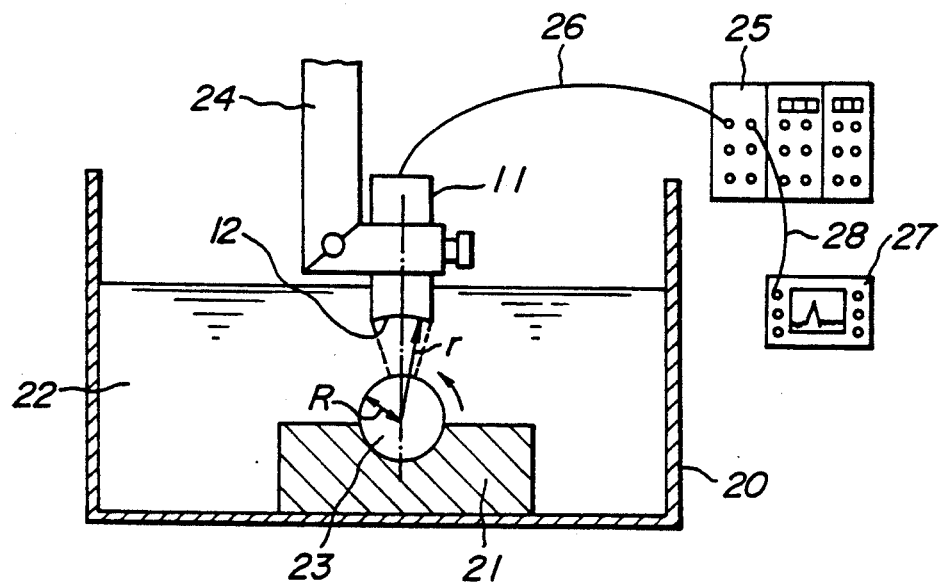
FIG. 9 is a diagrammatic view illustrating an example of ultrasonic testing method of the present invention.

Hereinafter, the present invention will be explained in more detail with examples.

EXAMPLE 1

An ultrasonic test was carried out by using an automatic scanning type ultrasonic testing apparatus as shown in FIG. 2.

A test block 1 having a dimension of 50×50×20 mm was made of silicon nitride. The automatic scanning type ultrasonic testing apparatus includes an ultrasonic flaw detector 2, a water tank 3, a scanning device 4 for slidably carrying a probe 6 and a plotter 5 electrically connected to the ultrasonic flaw detector 2 for outputting test results. The probe 6 is a water immersed focus type probe of a test frequency of 50 MHz and a focus of 25 mm, and is electrically connected to the ultrasonic flaw detector Further, a spectrum analyzer 7 is electrically connected to the ultrasonic flaw detector 2 by a high frequency cable for measuring frequency components of the echo.

First, the silicon nitride block 1 was set in the water tank 3 and the probe 6 was adjusted to be position just above the block. At this time, an echo reflected from the surface of the block was observed by th spectrum analyzer and it was confirmed that the central frequency was 50 MHz and the frequency components were ±30 MHz as shown in FIG. 1.

Next, the probe was scanned to automatically test the block, and several indications like flaws were detected on the plotter as shown in FIG. 3. Then, the position of the probe was adjusted on the silicon nitride block to position it at the location of the indication "A". At the location of the indication "A", the echo was observed by the spectrum analyzer and a waveform having three peaks at a frequency near 50 MHz and at frequencies of 30 MHz and 70 MHz as shown in FIG. 4 was obtained Also, the position of the probe was adjusted on the silicon nitride to position it at the location of the indication "B" and the echo was observed by the spectrum analyzer At the location of the indication "B", a waveform having a central frequency of 35 MHz and the high frequency component lower than the low frequency component as shown in FIG. 5 was obtained The two locations of indication "A" and "B" were marked on the silicon nitride block and the silicon nitride block was cut at these locations by means of a diamond cutter. It was found from this test that the indication "A" was a spherical hole shaped flaw as shown in FIG. 6a and the indication "B" was a crack as shown in FIG. 6b.

It is seen from the above example that the detected flaw is the crack when the reflected echo has a high frequency component lower than the incident ultrasonic wave, and is the hole when the reflected echo has peaks at the central frequency and its lower and higher frequency sides. Thus the condition of internal flaw in the test article can be decided by analyzing the frequency component of the reflected echo.

Accordingly, the ultrasonic testing method of the present invention makes it possible to decide a condition of an internal flaw in the article and to thereby decide whether the test article is acceptable for the purpose of using the article or not.

Referring to FIG. 7, a probe 11 has a curved tip surface 12 oppositely positioned to a curved incident surface 13 of a test article 14. The curved tip surface 12 is substantially the same kind of curved surface as the curved incident surface 13 such as a spherical surface. The radius of curvature "r" of the curved tip surface 12 may be 0.5 ~2.0 times, preferably 1.0 ~1.5 times that of the radius of curvature "R" of the curved incident surface 13. If the radius of curvature "r" of the curved tip surface 12 is smaller than 0.5 times the radius of curvature "R" of the curved incident surface 13 of the test article 14, the ultrasonic wave is focused near the curved incident surface 13 of the test article 14, as a result an internal flaw located inside of the curved incident surface is less detected While, if the radius of curvature "r" of the curved tip surface 12 is larger than 2.0 times the radius of curvature "R" of the curved incident surface 13 of the test article 14, the ultrasonic wave is scattered on the curved incident surface 13 and can not be transmitted into the test article 14, as a result the internal flaw can not be detected.

Referring to FIG. 8a, the probe 11 is provided with a connector 15 at the upper end thereof and a transducer 16 at the lower end thereof The transducer 16 has an acoustic lens 17 closely contacted to the surface thereof and is electrically connected to the connector 15 by a lead wire 18 passed through a dumper 19 in the probe.

The acoustic lens 17 is formed so as to provide the curved tip surface 12 having the same kind of the curved surface as that of the curved incident surface of the test article and the specific radius of curvature Referring to FIG. 8b illustrating another embodiment of the probe 11, in this embodiment, a transducer 16 is formed so as to provide the curved tip surface 12.

EXAMPLE 2

Eight kinds of ceramic balls made of silicon nitride having different diameter of 10 mm and 20 mm, each of which is provided with a hole of different diameter of 50, 100, 300 and 500 μm, respectively, were prepared.

An ultrasonic testing apparatus as shown in FIG. 9 was used. The testing apparatus includes a water tank 20 and a ball holder 21 immersed in water 22. The ball holder 21 is arranged so as to manually rotatably hold a ceramic ball 23 to be tested thereon The ceramic ball 23 was set in the ball holder 21, and a probe 11 of a test frequency of 50 MHz, with a transducer having a curved tip surface of a radius of curvature of 7.5 mm was set in a probe holder 24. The probe holder 24 was adjusted so as to position the probe 11 just above the ceramic ball 23. The probe 11 was electrically connected to an ultrasonic wave transmitter and receiver 25 by a high frequency cable 26. An oscilloscope 27 was electrically connected to the ultrasonic wave transmitter and receiver 25 by a high frequency cable 28 for observing an ultrasonic echo reflected from the ceramic ball 23.

Under the above circumstance, the oscilloscope was observed as the ceramic ball was manually rotated. After observing all around the surface of the ceramic ball, the ceramic ball was changed with the other. All the prepared ceramic balls were tested by repeating the aforementioned test. As the result of test, all flaws in the ceramic balls having the diameter of 10 mm could be detected, but the flaw of 50 μm in the ceramic ball having the diameter of 20 mm could not be detected.

Further, similar ultrasonic test were carried out by use of a probe of a test frequency of 50 MHz, with a transducer having a concave spherical tip surface of radius of curvature of 15 mm in the same manner as mentioned above. As the result of test, all flaws in the ceramic balls having the diameter of 20 mm could be detected, but only the flaw of 500 μm in the ceramic balls having the diameter of 10 mm could be detected Furthermore, similar ultrasonic test were carried out as comparative examples by use of a probe of test frequency of 50 MHz, with a plane transducer having a diameter of 5 mm in the same manner as mentioned above. As a result of the test, the flaw in all ceramic balls having both diameters of 10 mm and 20 mm could not be detected. The results of the aforementioned tests are shown in Table 1.

TABLE 1

| | Transducer tip | | Radius of ceramic ball R (mm) | r/R | Detected flaw size (μm) |
| --- | --- | --- | --- | --- | --- |
| | Kind of curved surface | Radius of curvature | | | |
| Invention 1 | concave spherical surface | 7.5 | 5 | 1.5 | all detected |
| | | | 10 | 0.75 | ≧φ100 |
| | concave spherical | 15 | 5 | 0.33 | only φ500 |
| | | | 10 | 1.5 | all detected |
| Comparative | flat | — | 5 | — | not detected |

TABLE 1-continued

| | Transducer tip | | Radius of ceramic ball R (mm) | r/R | Detected flaw size (μm) |
| --- | --- | --- | --- | --- | --- |
| | Kind of curved surface | Radius of curvature | | | |
| example | surface | | 10 | — | not detected |

EXAMPLE 3

Three cylindrical test pieces made of silicon nitride having a length of 50 mm and different diameters of 6, 10 and 20 mm were prepared. These test pieces were artificially provided with hole shaped internal flaws by embedding resin particles of different diameters of 50, 100, 300 and 500 μm in the test pieces at the time of molding.

Figure 10:
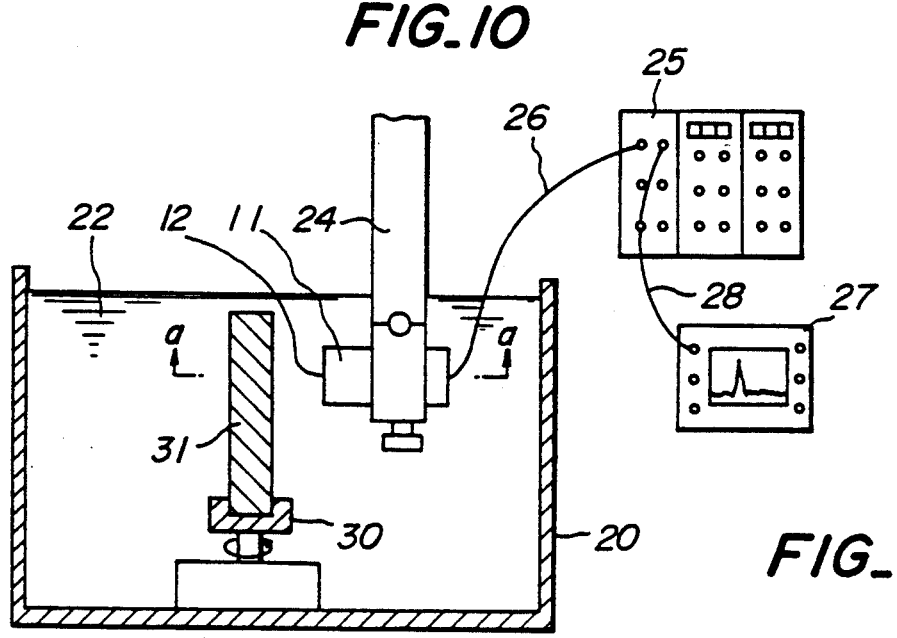
FIG. 10 is a diagrammatic view illustrating other example of ultrasonic testing method of the present invention.
Figure 11:
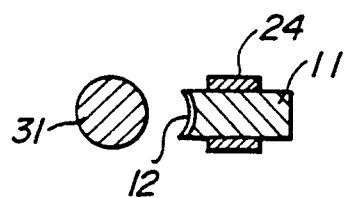
FIG. 11 is a sectional view taken along line a—a in FIG. 10 for showing a relationship of positions of a probe and a cylindrical test piece.

In this example, an ultrasonic testing apparatus shown in FIG. 10 was used. The ultrasonic testing apparatus includes a water tank 20 and a test piece holder 30 immersed in water 22. The test piece holder 30 is arranged so as to hold the cylindrical test piece 31 in a vertical position and rotate about a vertical axis.

The cylindrical test piece 31 was set in the holder 30 and the holder was adjusted such that an eccentricity of the cylindrical test piece relative to the axis of rotation of the holder does not exceed 0.1 mm.

A probe 11 of a test frequency of 50 MHz, with a transducer having a concave cylindrical tip surface of a radius of curvature of 10 mm was set in a probe holder 24 and the probe holder 24 was adjusted such that the axis of the probe is perpendicular to the axis of the cylindrical test piece 31 and the curved tip surface 12 of the transducer corresponds with the cylindrical surface 13 of the cylindrical test piece 31 in direction. The probe 11 was electrically connected to an ultrasonic wave transmitter and receiver 25 by a high frequency cable 26. An oscilloscope 27 was electrically connected to the ultrasonic wave transmitter and receiver 25 by a high frequency cable 28 for observing an ultrasonic echo reflected from the cylindrical test piece 31.

Under the above circumstance, the oscilloscope was observed as the cylindrical test piece was manually rotated. After observing all around the cylindrical surface of the cylindrical test piece, the cylindrical test piece was changed with the other All the three cylindrical test piece were tested by repeating the aforementioned test. As the result of the test, only a flaw of 500 μm in the test piece having the diameter of 6 mm could be detected, but flaws of diameter of at least 100 μm in the test piece having the diameter of 10 mm and all flaws in the test piece having the diameter of 20 mm could be detected.

Further, similar ultrasonic test were carried out by use of a probe of a test frequency of 50 MHz, with a transducer having a concave cylindrical tip surface of radius of curvature of 5 mm in the same manner as mentioned above. As the result of test, flaws having the diameter of at least 100 μm in the test pieces having the diameter of 6 mm and 20 mm were detected and all flaws in the test piece having the diameter of 10 mm were detected Furthermore, similar ultrasonic test were carried out by use of a probe of a test frequency of 50 MHz provided with a transducer having a diameter of 5 mm and a concave spherical tip surface of radius of curvature of 10 mm in the same manner as mentioned above. As a result of the test, a flaw having the diameter of 500 μm in the test piece having the diameter of 20 mm were detected, but the flaws in the test piece having the diameter of 6 mm and 10 mm could not be detected.

As a comparative example, similar ultrasonic test were carried out by use of a probe of a test frequency of 50 MHz provided with a flat transducer having a diameter of 5 mm. As a result of the test, the flaws in all the test pieces having the diameter of 6 mm, 10 mm and 20 mm could not be detected.

The results of the aforementioned tests are shown in Table 2.

TABLE 2

|  | Transducer tip | | Radius of ceramic test piece R (mm) | r/R | Detected flaw size (μm) |
| --- | --- | --- | --- | --- | --- |
|  | Kind of curved surface | Radius of curvature | | | |
| Invention 1 | concave cylindrical surface | 10 | 3 | 3.3 | only φ500 |
|  |  |  | 5 | 2.0 | ≧φ100 |
|  |  |  | 10 | 1.0 | all detected |
|  | concave cylindrical surface | 5 | 3 | 1.7 | ≧φ100 |
|  |  |  | 5 | 1.0 | all detected |
|  |  |  | 10 | 0.5 | ≧φ100 |
| Comparative example | concave spherical surface | 10 | 3 | 3.3 | not detected |
|  |  |  | 5 | 2.0 | not detected |
|  |  |  | 10 | 1.0 | only φ500 |
|  | flat surface | — | 3 | — | not detected |
|  |  |  | 5 | — | not detected |
|  |  |  | 10 | — | not detected |

It is seen from the above that the ultrasonic testing method of the second aspect of the present invention can detect very small internal flaws in a test article having a curved incident surface of a radius of curvature of at most several tens of millimeters by use of a probe having a curved tip surface of the same kind as that of the curved incident surface of the test article, and of a radius of curvature of 0.5 ~ 2.0 times that of the radius of curvature of the curved incident surface of the test article.

What is claimed is:

1. An ultrasonic testing method for detecting internal flaws in a test article, comprising the steps of:
   providing a test article having a concavely curved incident surface;
   providing an ultrasonic test probe having a concavely curved tip surface from which an ultrasonic wave is transmitted, said concavely curved tip surface being of the same shape as, and having a radius of curvature of 0.5 ~ 2.0 times that of said concavely curved incident surface of said test article; and
   transmitting an ultrasonic wave from said ultrasonic test probe to said test article to detect internal flaws in said test article.

2. The method of claim 1, wherein said test article has a spherical-shaped incident surface and said ultrasonic test probe has a spherical-shaped tip surface.

3. The method of claim 1, wherein said test article has a cylindrical-shaped incident surface and said ultrasonic test probe has a cylindrical-shaped tip surface.

* * * * *